(12) United States Patent
Riess et al.

(10) Patent No.: US 7,197,110 B2
(45) Date of Patent: Mar. 27, 2007

(54) METHOD FOR DETERMINING CHEMICAL CONTENT OF COMPLEX STRUCTURES USING X-RAY MICROANALYSIS

(75) Inventors: Michael Riess, Taunusstein (DE); Steven M. Scheifers, Hoffman Estates, IL (US); William L. Olson, Palatine, IL (US)

(73) Assignee: Motorola, Inc., Schaumburg, IL (US)

( * ) Notice: Subject to any disclaimer, the term of this patent is extended or adjusted under 35 U.S.C. 154(b) by 109 days.

(21) Appl. No.: 10/999,083

(22) Filed: Nov. 29, 2004

(65) Prior Publication Data

US 2006/0115042 A1    Jun. 1, 2006

(51) Int. Cl.
*G01N 23/223* (2006.01)
*G01N 23/06* (2006.01)

(52) U.S. Cl. .......................................... 378/45; 378/53
(58) Field of Classification Search ................. 378/44, 378/45, 51, 53
See application file for complete search history.

(56) References Cited

U.S. PATENT DOCUMENTS 5,027,132 A * 6/1991 Manns et al. ............... 347/225
5,249,216 A * 9/1993 Ohsugi et al. ................ 378/46
5,291,535 A * 3/1994 Baker et al. .................. 378/62
5,740,223 A * 4/1998 Ozawa et al. ................ 378/44
5,859,924 A * 1/1999 Liu et al. .................... 382/145
6,453,002 B1 * 9/2002 Mazor et al. ................ 378/49
6,825,645 B2 * 11/2004 Kelly et al. .................. 378/45
6,831,235 B1 * 12/2004 Enomoto et al. ........... 174/262
7,023,955 B2 * 4/2006 Chen et al. .................. 378/44
2003/0142781 A1 * 7/2003 Kawahara et al. ........... 378/44

* cited by examiner

*Primary Examiner*—Edward J. Glick
*Assistant Examiner*—Chih-Cheng Glen Kao

(57) ABSTRACT

A method for identifying hazardous substances in a printed wiring assembly having a plurality of discrete components, using micro X-ray fluorescence spectroscopy. A micro X-ray fluorescence spectroscopy (μ-XRF) and/or X-ray Absorption Fine Structure (XAFS) spectroscopy are used as detecting analyzers, to identify materials of concern in an electronic device. The device or assembly to be examined is analyzed by moving it in the X, Y, and Z directions under a probe in response to information in a reference database, to determine elemental composition at selected locations on the assembly, the probe positioned at an optimum analytical distance from each selected location for analysis. The determined elemental composition at each selected location is then correlated to the reference database, and the detected elements are assigned to the various components in the assembly.

17 Claims, 1 Drawing Sheet

METHOD FOR DETERMINING CHEMICAL CONTENT OF COMPLEX STRUCTURES USING X-RAY MICROANALYSIS

FIELD OF THE INVENTION

This invention relates generally to X-ray spectroscopy, and more particularly, to the automated use of X-ray spectroscopy to detect and identify specific metals in printed wiring assemblies.

BACKGROUND

Legislation in the European Union (EU) has been enacted to reduce the level of hazardous chemicals in the environment. The Restriction of certain Hazardous Substances (RoHS) act has targeted materials such as lead, cadmium, mercury, chromium VI and some brominated flame retardants used in electronic devices. In order to comply with these enacted regulations, a method to detect and identify these and other hazardous materials in electronic devices is needed. Such a method should be fast and accurate to enable rapid testing and short turnaround times in keeping with the 'time to market' requirements of the global electronics industry. The detection method also needs to be highly cost effective and it should not have any adverse impact on the environment by using other hazardous substances in the detection procedure.

BRIEF DESCRIPTION OF THE DRAWINGS

The features of the invention believed to be novel are set forth with particularity in the appended claims. The invention itself however, both as to organization and method of operation, together with objects and advantages thereof, may be best understood by reference to the following detailed description of the invention, which describes certain exemplary embodiments of the invention, taken in conjunction with the accompanying drawings in which:

The sole drawing figure is a flow chart depicting decision tree analysis methods consistent with certain embodiments of the present invention.

DETAILED DESCRIPTION

Figure 1:
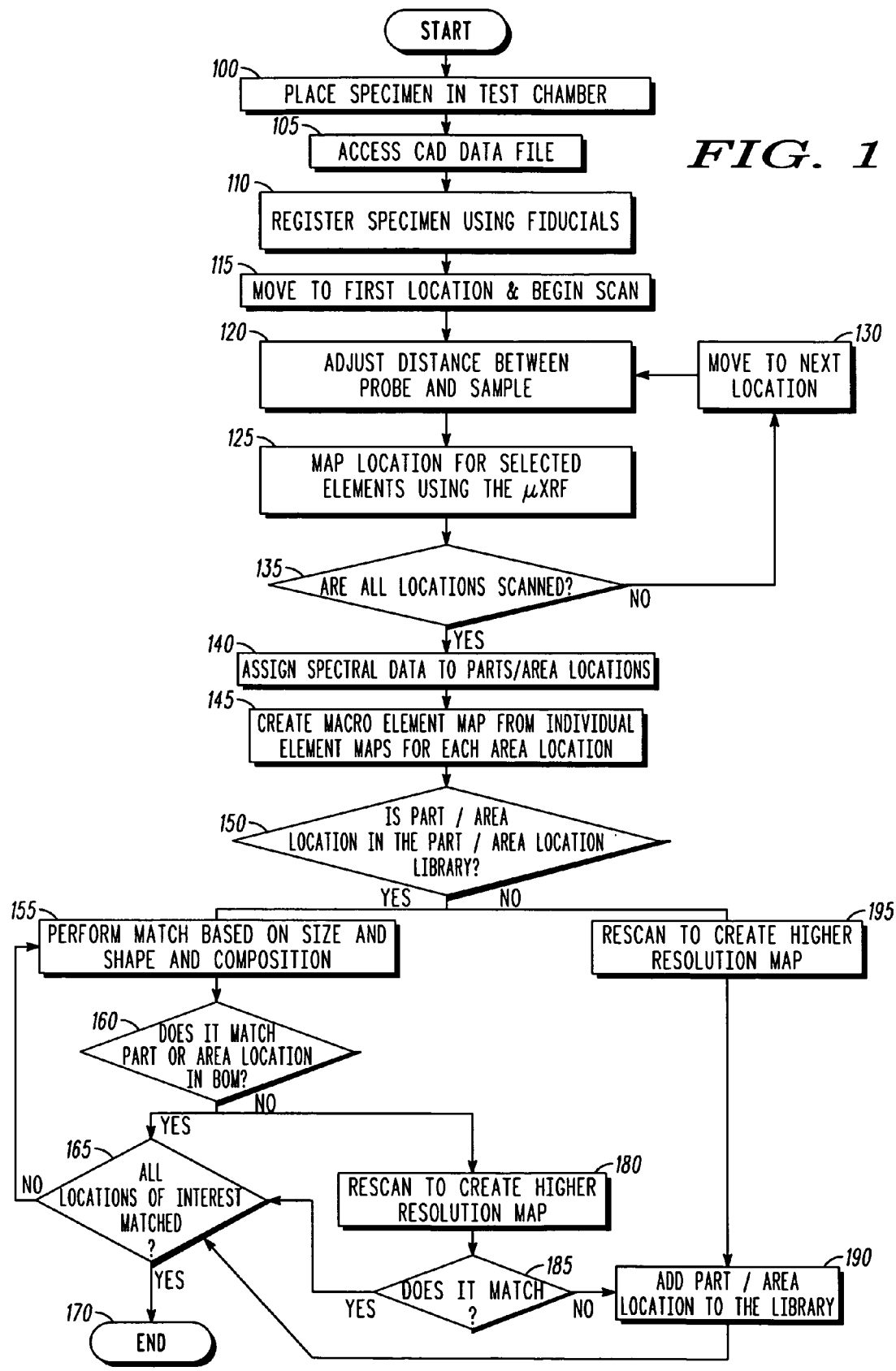

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to describe the same, similar or corresponding elements in the drawings. Electronic devices, printed wiring assemblies (PWA), and individual components historically have sometimes contained materials of concern such as Pb, Cr, Cd, Hg and Br. The disclosed embodiments employ micro X-ray fluorescence spectroscopy (µ-XRF) and X-ray Absorption Fine Structure (XAFS) spectroscopy as detecting methods, to localize those and other materials of concern in an electronic device. The device or assembly to be examined is analyzed by moving it in the X, Y, and Z directions under a probe in response to information in a reference database, to determine elemental composition at selected locations on the assembly, the probe positioned at an optimum analytical distance from each selected location for analysis. The determined elemental composition at each selected location is then correlated to the reference database, and the detected elements are assigned to the various components in the assembly.

In the descriptions below, we utilize the term "printed wiring assembly" or "PWA" for convenience, but it is to be understood that use in this manner is not intended to be limiting, but is intended to cover these as well as other types of complex assemblies used in present and future electronic devices, such as, but not limited to, motors, cable assemblies, displays, switches, knobs, housings, speakers, transducers, etc. Referring now to FIG. 1, a flow chart depicting one embodiment of the invention, the specimen or sample to be analyzed for presence of hazardous chemicals is placed 100 directly in the chamber of a µ-XRF or XAFS analyzer. The method allows fast detection and identification because there is no sample preparation such as sputtering, that might use other environmentally critical materials. A computer aided design (CAD) data file for the sample is then accessed 105. The CAD file contains (among other things) a mathematical representation of the physical dimensions of the various components on the PWA, and their locations on the printed circuit board, and is used as a reference database in the analysis. CAD databases and the information they typically contain are well known to those skilled in the art of design and assembly of electronic devices, and will not be further elaborated upon here. The CAD database is ported to a controller in the µ-XRF or XAFS analyzer to enable some of the functions of the analyzer to be driven by the information in the file. Typically, the stage of the analyzer is moved in response to information in the CAD database so as to move the sample about, so that the analyzer probe can 'see' all the necessary regions of the sample. The location of the sample with respect to the analyzer is then determined by registering it 110 using datum marks or fiducials. Although this is optional and can be performed either manually or automatically, we find it most useful to achieve complete automation and use the datum information typically located in the CAD database to register the sample. Registration using datums is known to those skilled in the art, and mechanism such as optical scanning, laser registration, mechanical registration, etc. can be employed with success here. The sample is then moved 115 to the first location that will be analyzed or scanned, by moving the analyzer stage appropriately in the x and y axes. Typically, many, if not all, of the components on a PWA are different size and shape, and when using X-ray analysis techniques, it is critical for accurate analysis to maintain the proper distance between the area to be analyzed on the sample and the probe on the analyzer. This optimum analytical distance is achieved by adjusting or moving the sample stage sufficiently in the z axis 120 so that the proper distance between the probe and the analysis area is made. The distance between the sample and the probe is determined by an altimetry sensor, such as a video camera, a Hall effect sensor, a sensor that uses triangulation, or other optical means. In accordance with certain embodiments, the probe is moved automatically during the analysis so that the probe-sample distance is always at the optimum distance during the analysis period.

Depending on the resolution desired in the analysis, various beam sizes can be used. Larger beam sizes typically yield lower resolution, but cover a larger area. As in most analytical procedures, one must choose between resolution and coverage area, as needed. In the case of analyzing using µ-XRF, the chemical elements in the surface area respond to the excitation energy of the beam and emit secondary photons which are detected by the analyzer detector. Once the analytical parameters are selected, the analysis is performed 125 in conventional manner, and the detected elements of interest (if any are found) are temporarily stored in memory in the analyzer's computer or in another storage area.

After the first location is analyzed 125, the stage is driven by information in the CAD database to move the sample to the next location 130. Note that in certain embodiments, the CAD database does not directly move the stage, but instead the controller in the µ-XRF analyzer responds to information in the database. Alternate embodiments allow the CAD database to directly control the stage movement. The optimum analytical distance is again attained by adjusting or moving the sample stage sufficiently in the z axis 120 so that the proper distance between the probe and the analysis area is made, and an analysis of the second location is made 125 as previously explained. After the second location is analyzed, the stage is driven by information in the CAD database to move the sample to the next location 130. Blocks 120, 125, and 130 are repeated as necessary (as shown by the loop in the flow diagram) until all locations of interest on the sample are analyzed. After the last location is analyzed 135, the information from the multiple stages of analysis is correlated 140 to the information in the CAD database so as to assign the level of the various elements detected to the various components in the PWA. The spectral data obtained at each respective location during all of the scans is assigned to specific locations or components by assigning the spectral data to one or more components or locations. An elemental map of the scanned area or component can also be created 145 that shows the presence or absence of each element as a function of the topography of the sample, where the various components on the PWA are shown and the level of each detected element can be overlaid on the CAD diagram.

After the elemental map has been created 145, the CAD database is queried to determine whether or not the scanned area or component is resident in the database (block 150). If the area of interest is stored in the database (as indicated by the 'yes' branch in the diagram immediately below box 150), then the information derived from the scan is compared 155 to that stored in the database using 90%, 95%, or 99% probability match statistical techniques. The elemental map and three dimensional component geometric information provides a tool with which to compare or match the component on the sample to a component resident in the database, since information relating to component size and shape and chemical composition is contained in the CAD database. For example, the elemental map may indicate that a certain resistor on the sample being scanned possesses copper terminations, a resistive element that contains nickel and chromium and has a ceramic base made of silicon dioxide. This information, combined with information relating to the size and shape of the resistor, can be matched to information in the database to determine the exact part number and resistive value of the resistor, using statistical matching techniques. A decision is made as to whether or not it matches the information stored in a bill of materials (BOM) database 160, and if the answer is 'yes' then another scanned location or component is selected 165 and the process of blocks 155, 160, and 165 are repeated until complete, at which point the analysis ends 170. If the answer to the match decision at block 160 is 'no', then that area or component of interest is rescanned 180 at a higher resolution to create a more detailed or in-depth analysis. A comparison of the information that was obtained from the rescan is again made to the bill of material database 185, and if a match is made, then the analysis moves to another location in block 165, and continues from there as previously. If the answer is 'no' (i.e. not a match), then the information from the rescan is added to the CAD database 190 to create a new component or area location for reference when another sample is analyzed in the future.

Returning now to block 150, the situation where the CAD database is queried to determine whether or not the scanned area or component is resident in the database, if the answer is 'no', then the area or component of interest is rescanned 195 at a higher resolution to create a more detailed or in-depth analysis, and the information from the rescan is added to the CAD database 190 to create a new component or area location for reference when a future sample is analyzed.

Having now described one embodiment, we now present additional details on the equipment and technique used. This disclosure is presented by way of further educating the reader in some details of the procedure, and not by way of limitation. For elemental mappings, a microbeam XRF System Eagle II µ-Probe (Röntgen-analytik Messtechnik GmbH, Taunusstein, Germany) was used, fitted with a 40 Watt rhenium tube (40 kV, 1000 µAmp) and a 100 µm capillary optic. The samples (assemblies from a cellular telephone) were placed onto the computer controlled stage of the instrument and vacuum was drawn. With two video microscopes (1:10 and 1:100 magnification), the area for the elemental mapping was selected and subsequently the desired elements were selected. The scans of printed wiring boards with an aspect ratio of 5:2 (length:width) were performed in two separate measurements, and front and back sides were examined. For elements up to an atomic number 42 (Mo), K-radiation lines were used for analysis. Heavier elements were detected using L-radiation lines. For the determination of Bi and Hg, M-radiation lines were used in addition. The selected elements were: silver, arsenic, bismuth, bromine, cadmium, chromium, mercury, nickel, lead, antimony, and tin. The measurement time for one reading point was set to 200 milliseconds and the matrix size was set to 256×200. From all single spectra, a total spectrum was compiled and element distribution plots were calculated by software (Vision XRF Software for Eagle II µ-Probe, Version 3.308). Light areas in the plot corresponded to sections of high element concentration. Elemental Maps are extracted from the µ-XRF measurements for each element of concern from the measurements and converted to black and white maps. These are laid over the board drawing information to determine which parts contain what elements. This is done for all elements of interest. The intensity at each measurement point where an element of concern is detected is correlated to the type of part. From a calibration for each type of part the contribution to the concentration of the element of concern is made. The result of an elemental distribution analysis is recorded in a total spectrum, i.e. all single spectra obtained from measured spots are added. In addition element pictures for every chosen element are calculated from the measured data. Thereby, element intensities are mapped as more or less intensive colors.

A suitable procedure for evaluation of the data obtained was defined including correlation of the data obtained from measurement and the number of components on the PWB investigated being not compliant to the given legal regulations. Some of the advantages that accrue to this novel method are: The method described is capable of processing a broad variety of PWBs with the mounted components in a single analysis. The method makes it possible to localize elements other than Br and Pb making use of subtraction of spectra or other means. The new process has much lower cost and is much faster compared to classical techniques. The complete system is automated and allows direct detection of parts that are incompliant with environmental regulations. Corrective action can be requested from the suppliers based on the results and detection of incompliant parts. Overall the detection and localization of heavy metals and brominated compounds in populated PWB is made easier, more time effective and less costly through this approach, with no sample preparation and the use of comparably inexpensive analytical detection methods.

In summary, without intending to limit the scope of the invention, the disclosed embodiments provide a method of checking printed wiring assemblies or other complex structures used in electronic devices for compliance with the RoHS Act. The XRF allows using bromine as an indicator element for identification of brominated flame retardant additives such as octabromodiphenyl, decabromodiphenyl, octabromodiphenyl oxide, decabromodiphenyl oxide, and tetrabromobisphenol A and chromium as an indicator element for Cr VI.

While the invention has been described by citing specific details and parameters used in actual analyses, it is to be understood that these are offered by way of example, and not by way of limitation, and variation from these settings and values may most certainly occur and still fall within the scope and spirit of the invention. It is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

What is claimed is:

1. A method for identifying hazardous substances in a printed wiring assembly having a plurality of discrete components, using micro X-ray fluorescence spectroscopy, comprising:
   a) analyzing the printed wiring assembly by moving a probe over the assembly in response to information in a reference database, to determine elemental composition at selected locations on the printed wiring assembly, the probe positioned at a substantially optimum analytical distance from each selected location for analysis; and
   b) correlating the determined elemental composition at the selected locations to the reference database, to assign detected elements to the various components on the printed wiring assembly.

2. The method of claim 1, wherein the probe is maintained at the substantially optimum analytical distance by means of an altimetry sensor.

3. The method of claim 2, wherein the altimetry sensor comprises a video camera, a Hall effect sensor, or a triangulation sensor.

4. The method of claim 1, wherein the probe is maintained at the substantially optimum analytical distance in response to information in the reference database describing the printed wiring assembly topography.

5. The method of claim 1, further comprising initially registering the printed wiring assembly relative to the probe by means of one or more datum locations on the printed wiring assembly.

6. A method of scanning X-ray microanalysis, comprising:
   a) providing a sample having a surface topography of varying heights;
   b) analyzing the sample using micro X-ray fluorescence spectroscopy, wherein a probe is moveable in X, Y, and Z axes, and wherein movement in the Z axis is performed to maintain the probe at a substantially optimum analytical distance from the sample at each of the varying sample heights; and
   c) wherein the X and Y probe movements are responsive to a database containing information relating to various locations on the sample, to enable elements detected in the sample to be correlated to the information in the database.

7. The method of claim 6, wherein the probe is maintained at the substantially optimum analytical distance by means of an altimetry sensor.

8. The method of claim 7, wherein the altimetry sensor comprises a video camera, a Hall effect sensor, or a triangulation sensor.

9. The method of claim 6, wherein the probe is maintained at the substantially optimum analytical distance in response to information in the reference database describing the surface topography.

10. The method of claim 6, further comprising, after (a), registering the sample relative to the probe by means of one or more datum locations on the sample.

11. The method of claim 6, wherein the sample is a printed wiring assembly having a plurality of discrete components.

12. A method for microanalysis, comprising:
   a) providing a sample having a surface topography of varying heights;
   b) placing the sample in an analysis chamber;
   c) analyzing the sample at a plurality of locations by means of a probe that is responsive to a reference database, wherein the probe is movable in X, Y, and Z axes, and wherein movement in the Z axis is performed to maintain the probe at an optimum analytical distance from the sample at each of the plurality of locations; and
   d) wherein information from the analysis performed in (c) is correlated to each of the plurality of locations in the database.

13. The method of claim 12, wherein the probe is maintained at the optimum analytical distance by means of an altimetry sensor.

14. The method of claim 13, wherein the altimetry sensor comprises a video camera, a Hall effect sensor, or a triangulation sensor.

15. The method of claim 12, wherein the probe is maintained at the optimum analytical distance by means of correlating the X and Y movements of the probe to a database containing reference information about the sample topography.

16. The method of claim 12, wherein the sample is a printed wiring assembly with a plurality of discrete components.

17. The method of claim 12, further comprising, after (b), registering the sample relative to the probe by means of one or more datum locations on the sample.

* * * * *